US011311311B2

(12) United States Patent
Sperry et al.

(10) Patent No.: US 11,311,311 B2
(45) Date of Patent: Apr. 26, 2022

(54) DEVICES AND METHODS FOR GUIDING A SURGICAL INSTRUMENT

(71) Applicant: Boston Scientific Scimed, Inc., Maple Grove, MN (US)

(72) Inventors: Erik E Sperry, Newburyport, MA (US); Jerry T Long, Jamaica Plain, MA (US); Ronald Ciulla, Westford, MA (US); Timothy P Harrah, Cambridge, MA (US); Aaron K Kirkemo, Gladstone, NJ (US); Mark A Hera, Holden, MA (US); Kenneth P Reever, Hopedale, MA (US); Brandon W Craft, Edgewater, MD (US); Elizabeth A Stokley, Baltimore, MD (US); Sebastian Koerner, Berlin (DE); Chad Schneider, Owings Mills, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 481 days.

(21) Appl. No.: 15/400,214

(22) Filed: Jan. 6, 2017

(65) Prior Publication Data
US 2017/0196590 A1     Jul. 13, 2017

Related U.S. Application Data

(60) Provisional application No. 62/276,569, filed on Jan. 8, 2016.

(51) Int. Cl.
*A61B 17/34*     (2006.01)
*A61B 17/28*     (2006.01)
(Continued)

(52) U.S. Cl.
CPC ...... *A61B 17/3403* (2013.01); *A61B 17/2816* (2013.01); *A61B 2017/3407* (2013.01);
(Continued)

(58) Field of Classification Search
CPC ......... A61B 90/10; A61B 90/11; A61B 90/14; A61B 90/39; A61B 2090/101;
(Continued)

(56) References Cited

U.S. PATENT DOCUMENTS 4,809,694 A * 3/1989 Ferrara .............. A61B 17/3403
606/130
5,354,283 A * 10/1994 Bark .................... A61M 25/02
128/DIG. 26

(Continued)

FOREIGN PATENT DOCUMENTS

DE        19808220 A1     9/1999
DE     102011109185       1/2013
(Continued)

OTHER PUBLICATIONS

International Search Report and Written Opinion dated Sep. 1, 2017, for PCT/US2017/012476 (22 pages).

*Primary Examiner* — Darwin P Erezo
*Assistant Examiner* — Christian D Knauss
(74) *Attorney, Agent, or Firm* — Seager, Tufte & Wickhem, LLP

(57) ABSTRACT

Devices for guiding an instrument into a body of a patient, at a targeted point of entry and along an insertion path at a targeted insertion angle, are described herein, such as a guide for an access needle in a PCNL procedure for accessing the kidney to remove kidney stones, the devices comprising a base component, a guide assembly, and optionally an insertion mechanism. The base component is aligned in use with the point of entry and the guide assembly cooper-
(Continued)

ates with the base component to allow for the instrument to be aligned and fixed at any circumferential angle around an axis perpendicular to the point of entry and at any vertical angle ranging from 0 to 45 degrees away from the axis in a direction toward the body. The optional mechanism allows for mechanical insertion once the instrument is aligned and fixed. Devices and methods disclosed herein allow a medical professional to accurately and stably guide an instrument at a targeted point and angle and to a desired depth, while minimizing the exposure to radiation in the surgical field that is used to image the insertion path.

14 Claims, 10 Drawing Sheets

(51) Int. Cl.
*A61B 34/20* (2016.01)
*A61B 90/00* (2016.01)

(52) U.S. Cl.
CPC .............. *A61B 2017/3409* (2013.01); *A61B 2034/2051* (2016.02); *A61B 2090/0811* (2016.02)

(58) Field of Classification Search
CPC ........ A61B 2090/103; A61B 2090/363; A61B 2090/3954; A61B 2090/3966; A61B 2090/3983; A61B 17/3403; A61B 2017/3407; A61M 25/02; A61M 2025/0213; A61M 2025/0233; A61M 2025/0246; A61M 2025/0266; A61M 2025/028; A61M 2025/0286
See application file for complete search history.

(56) References Cited

U.S. PATENT DOCUMENTS

| | | | |
|---|---|---|---|
| 5,375,588 A * | 12/1994 | Yoon | A61B 17/3403 600/114 |
| 6,039,725 A * | 3/2000 | Moenning | A61B 17/34 604/108 |
| 6,689,142 B1 | 2/2004 | Tremaglio, Jr. et al. | |
| 7,204,826 B2 | 4/2007 | Tremagiio et al. | |
| 8,888,787 B2 | 11/2014 | Wynberg | |
| 8,998,943 B2 | 4/2015 | Baldwin et al. | |
| 9,095,361 B2 | 8/2015 | Baldwin | |
| 2003/0040753 A1 * | 2/2003 | Daum | A61B 17/3403 606/96 |
| 2007/0016067 A1 | 1/2007 | Webster et al. | |
| 2010/0191259 A1 | 7/2010 | Suzuki et al. | |
| 2012/0190970 A1 | 7/2012 | Velusamy et al. | |
| 2012/0253361 A1 | 10/2012 | Drstvensek et al. | |
| 2013/0197534 A1 | 8/2013 | Lauderbaugh et al. | |
| 2014/0276559 A1 * | 9/2014 | Page | A61B 17/3403 604/506 |

FOREIGN PATENT DOCUMENTS

| | | |
|---|---|---|
| EP | 2193750 A1 | 6/2010 |
| EP | 2567668 A1 | 3/2013 |
| WO | 2004021898 A1 | 3/2004 |
| WO | 2011053259 A1 | 5/2011 |
| WO | 2012063267 A2 | 5/2012 |
| WO | 2013110973 A1 | 8/2013 |
| WO | 2014194146 A2 | 12/2014 |

* cited by examiner

DEVICES AND METHODS FOR GUIDING A SURGICAL INSTRUMENT

CROSS-REFERENCE TO RELATED APPLICATIONS

This application claims the benefit of priority to U.S. Provisional Application Ser. No. 62/276,569, filed Jan. 8, 2016, the disclosure of which is herein incorporated by reference in its entirety.

FIELD OF THE INVENTION

The present disclosure relates generally to devices and methods for guiding a surgical instrument, particularly to needle guides for percutaneous access to a surgery site, and more particularly to needle guides to aid in access to the kidney as part of a PCNL procedure to treat kidney stones.

BACKGROUND

Many medical procedures are undertaken through narrow insertion paths from outside the body of a patient to a target area in the body, in order for the diagnosis and/or treatment of a variety of diseases and conditions. These procedures may be minimally invasive. Percutaneous access is a commonly used step in such procedures. In order to create an insertion path from a percutaneous point of entry to a target area, an instrument such as an access needle typically is inserted as an initial step. As further steps in the procedure, a guidewire may be placed through the instrument to the target area and, after removal of the instrument, the insertion path may be enlarged to accommodate other medical devices necessary for the procedure. Antegrade access and placement of a needle through the skin into one of the calyces of the kidney during a percutaneous nephrolithotomy ("PCNL") is an example of such a procedure.

One type of PCNL procedure utilizes a triangulation technique with an access needle that is 18 to 21 gauge, an x-ray emitting device and a fluoroscope. The medical professional first aligns the tip of the needle (on the patient's back) with the target calyx (visualized by injecting a radiopaque dye into the kidney) in a vertical position with the x-ray head and the fluoroscope also in the vertical position defining the needle's point of entry. The term "vertical" as used in this context means an axis extending perpendicular from the point of entry. When the needle is in a vertical position, it can be aligned along this axis with the x-ray head and the fluoroscope at certain points of the procedure. The medical professional will then re-position the x-ray head and the fluoroscope to a 30 degree angle from the vertical position while keeping the needle in the vertical orientation (or at a slight angle from the vertical position). By using the x-ray head and the fluoroscope in the vertical and 30 degree positions and viewing the needle on a display associated with the fluoroscope, the medical professional will approximate the targeted insertion angle to reach the target calyx as well as the desired needle depth. The medical professional then pushes the needle through the entry point, towards the target calyx. As necessary, the medical professional moves the x-ray head and the fluoroscope between the two views and the needle insertion angle can be adjusted. Typically, multiple rounds of angle adjustment are necessary in order to achieve access and the process is time consuming. The medical professional uses tactile feedback and imaging to determine when the target calyx has been reached by the tip of the needle. A final check to confirm access is performed by attaching a syringe to the needle and aspirating. If urine is not aspirated, kidney access has not been achieved and the needle must be repositioned.

A second technique for performing a PCNL procedure is known as the "bullseye" technique. A patient is typically oriented on his/her side at an angle to an operating table such that a target calyx is generally aligned with the operating table (for example, the calyx is perpendicular to the table). A medical professional attempting kidney access with this technique will typically first align a guide needle on the patient's back with the target calyx (visualized by injecting a radiopaque dye into the kidney) using the x-ray head and the fluoroscope in vertical position, defining the targeted point of entry. The medical professional will then insert the guide needle, for example a 13 gauge needle, vertically through this entry point and about 2-3 cm into the patient's fatty tissue layers. This needle acts as the guide for an entry needle. A physician typically will clamp a pair of forceps around the 13 gauge needle and hold the forceps at their proximal end, allowing the physician to adjust the orientation of the 13 gauge needle while keeping his/her hands out of the fluoroscopy field. When the medical professional has aligned the radiopaque hub of the 13 gauge needle with the target calyx, and with the x-ray head and the fluoroscope in vertical orientation, an 18 gauge entry needle is inserted through the 13 gauge needle into the patient's kidney. A properly aligned guide needle, which can have a radiopaque outer wall, will appear in the screen display of the fluoroscope as a circle that circumscribes at least a portion of a target calyx with an entry needle, which also can be radiopaque, in the center of the circle. Tactile feedback and aspiration to confirm urine is also used with this technique. This technique like the triangulation technique can be time-consuming as it may require multiple attempts at positioning the entry needle.

Initial access, such as with the PCNL targeting techniques, is often one of the most difficult steps of the procedure. Even with real-time, imaging guidance with ultrasound, CT, or fluoroscopy, due to the depth of the tissues that may surround a target location (e.g., the kidney) and the variation of the anatomy (for example, shifting of the renal position caused by breathing), medical professionals are asked to hit a small moving target positioned at a depth inside the body. A slight error in alignment may result in failure to access the desired target location. In an attempt to maintain proper alignment, medical professionals tend to grasp the instrument directly using their hands (placing their hands in the field of radiation) or grasp it indirectly using a rudimentary holder. This may result not only in the insertion angle shifting, which can affect the accuracy of the intended insertion path, but standard imaging fluoroscopy accounts for significant procedural radiation exposure to the patient as well as the surgical team. The amount of fluoroscopy required to obtain instrument access can be significant and over time with multiple procedures performed may lead to significant radiation exposure approaching or exceeding the recommended yearly occupational exposures of radiation.

A need therefore exists for more accurate, straightforward and stable devices and methods that allow a medical professional to guide an instrument at a targeted entry and angle and to a desired depth along an insertion path, while minimizing the exposure to radiation in the surgical field that is used to image the insertion path.

SUMMARY

The present disclosure allows for the positioning and insertion of an instrument, such as an access needle, into the body of a patient. Some advantages that may be realized by the devices, systems and methods of the present disclosure, including the various exemplary embodiments described herein, include shortening the length of a procedure, allowing for more precise positioning of the instrument in relation to a target, reducing trauma to tissue from repeated attempts to properly insert the instrument and providing a stable platform for insertion, all of which may help to reduce the time that medical professionals performing procedures have their hands exposed to a radiation field.

In one aspect of the disclosure, a device for guiding the insertion of an instrument having a longitudinal axis into a body of a patient at a targeted point of entry and along a path at a targeted insertion angle comprises: a base component configured to be oriented and fixed in a first position, wherein the first position correspond to the targeted point of entry; and a guide assembly, the assembly having a first element cooperating with the base component to orient the instrument with respect to the first position, a second element configured to be oriented and fixed in a second position, wherein the second position corresponds to the targeted insertion angle, and a third element configured to translate the insertion angle to the instrument as it guides the instrument along the longitudinal axis into the body. In some embodiments, a base component comprises a base rod having a distal end and at least one leg having a distal surface, the base rod aligning the longitudinal axis of the instrument parallel to the base rod during insertion, the at least one leg extending perpendicular from the distal end of the base rod to a terminal end, the distal surface of the at least one leg providing stable engagement of the device against the body during insertion. In other embodiments, a terminal end comprises a through-hole that is configured to slidingly engage the instrument at a first position during insertion. In further embodiments, a base component comprises a base rod extending distally to at least one leg extending perpendicular to the base rod, a guide assembly comprises a shaft extending perpendicular to the base rod, a first element comprises an end effector at a distal end of the shaft configured to reversibly engage and maintain the instrument at a first position during insertion, wherein the third element comprises a guide component at a middle portion of the shaft that couples the shaft in sliding relationship along the base rod, and wherein the second element comprises a handle at a proximal end of the shaft, the handle configured to be grasped by a user to position and maintain the device at the first and second position and to slide the shaft along the base rod.

In another aspect of the disclosure, a guide assembly comprises a shaft including a first arm at a distal end portion of the shaft, the first arm in cooperative arrangement with a second arm as the base component at the distal end portion of the shaft, the first arm including an end effector as the first element configured to reversibly engage an instrument, the second arm including a through-hole configured to slidingly engage the instrument, the first and second arms aligning the longitudinal axis of the instrument perpendicular to the shaft, the shaft including an articulating component as the third element joining the first and second arms, and the shaft including a handle component as the second element at a proximal end of the shaft, the handle configured to be grasped by a user to position and maintain the device at the first and second position. In some embodiments, a device further comprises an insertion mechanism, wherein a handle includes an actuation device, the insertion mechanism connecting the actuation device, an articulating component and first and second arms in cooperative relationship to each other. During insertion of an instrument, actuating the actuation device at the handle causes the first arm engaging the instrument to move toward the second arm. In some embodiments, an end effector comprises a clamping mechanism.

In other aspects of the disclosure, a guide assembly comprises three or more legs having a distal end and a proximal end, each leg having one or more feet as the base component extending radially from the distal end of the legs, the feet providing stable engagement of the device against the body during insertion, a collar as the first element joining the proximal ends of the legs together and including a through-hole configured to slidingly accommodate an instrument therethrough, each of the legs including portions adjustable in length as the second element, and an alignment device as the third element, whereby independent adjustment of the length of the legs and guiding the instrument through the collar and alignment device, positions and maintains the device at the first and second position. In some embodiments, an alignment device comprises a second collar positioned at a middle portion of device legs and aligned longitudinally with the collar at the proximal end of the legs In another aspect of the disclosure, a base component comprises a proximal and distal surface, a lumen extending therethrough is aligned in a first position during insertion, the distal surface configured to provide stable engagement of the device against the body during insertion, a guide assembly removably engageable with the proximal surface of the base component, a first element including a first guide hole in fixed alignment with the lumen of the base component, a third element including a second guide hole configured to slidingly accommodate the instrument in alignment with the first guide hole and the lumen of the base component during insertion, and a second element comprises the first guide hole and the second guide hole and a mechanism to adjust and fix the second guide hole relative to the first guide hole in a second position. In some embodiments, a second element comprises a flexible member including a longer arm portion and a shorter arms portion in a Y-shape, a middle of the longer arm portion including the first guide hole and engageable with the base component to align the first guide hole and the lumen at the first position, the shorter arms portion including the second guide hole and flexible portion that is bendable back over the longer arm portion and fixable to the body in order to align the second guide hole relative to the first guide hole in the second position.

In a further aspect of the disclosure, a second element and a proximal surface of a base component comprise a ball and socket arrangement, a ball of the second element including a first guide hole and a second guide hole in linear alignment and together forming a through lumen in the ball in alignment with a lumen of the base component, the ball adjustable in the socket to align the through lumen to a second position. In some embodiments, a mechanism of the second element comprises a moveable engagement member configured to be pushed or pulled to frictionally fix the second element to the second position. In some embodiments, a device further comprises an insertion mechanism affixed to a guide assembly, the insertion mechanism including an instrument holder, flexible wing portions and an insertion member, the wings portions extending at one end from the sides of the guide assembly to another end fixed at sides of the instrument holder, the insertion member in operable arrangement with the instrument holder and wing portions, whereby movement of the insertion member flexes the wing portions and moves the instrument holder toward the base component and guide assembly in alignment with a first position and a second position.

In another aspect of the disclosure, the alignment of a second element, such as a second guide hole, relative to a first element, such as a first guide hole, at a second position may be at any circumferential angle ranging from 0 to 360 degrees around an axis perpendicular to a first position, depending on the relative position of the user with respect to the patient and the necessary orientation of the instrument with respect to the first position or targeted point of entry and the second position or targeted insertion angle, and at any vertical angle ranging from 0 to 45 degrees away from such axis in a direction toward the body, which in practice may more typically fall within the range of 15-45 degrees or 15-30 degrees from vertical, but again any angle in the range may be suitable depending on the necessary orientation of the instrument with respect to the second position or targeted insertion angle.

In a further aspect of the disclosure, a base component and guide assembly comprise an integrated hub unit, the base component of the hub unit is removably engageable with a proximal end of an instrument, a first element comprises an exterior surface of the hub unit configured to be grasped by a user to orient the hub unit and instrument to a first position, a second element comprises an electronic position sensing mechanism within the hub unit configured to be reversibly set to a second position, a third element comprises a visual display on the hub in operative arrangement with the electronic position sensing mechanism and configured to alert the user during insertion if the longitudinal axis of the instrument is guided outside of a linear axis defined by the first and second position.

In another aspect of the disclosure, a system for establishing guided access into the body of a patient at a targeted point of entry and along a path at a targeted insertion angle, comprises: an instrument having a longitudinal axis; a base component configured to be oriented and fixed in a first position, wherein the first position correspond to the targeted point of entry; and a guide assembly, the assembly having a first element cooperating with the base component to orient the guide assembly with respect to the first position, a second element configured to be oriented and fixed in a second position, wherein the second position corresponds to the targeted insertion angle and is linearly aligned with the first position, and a third element configured to translate the insertion angle to the instrument and guide the instrument into the body with the longitudinal axis corresponding to the path.

In another aspect of the disclosure, methods of guided access of an instrument into the body of a patient at a targeted point of entry and along a path at a targeted insertion angle comprise the steps of placing a device at the point of entry, the device comprising a base component and guide assembly, the guide assembly having a first element and second element cooperating with the base component; aligning the base component to a first position corresponding to the point of entry; orienting the second element, in linear alignment with the first element, to a second position corresponding to the targeted insertion angle; fixing the device at the second position; and inserting the instrument through the device, the device guiding the instrument into the body with the longitudinal axis of the instrument following the linear alignment of the first and second element at the second position. In some embodiments, the step of orienting the second element, in linear alignment with the first element, to a second position can be as described above at any circumferential angle ranging from 0 to 360 degrees around an axis perpendicular to the first position and at any vertical angle ranging from 0 to 45 degrees away from such axis in a direction toward the body. In some embodiments, the step of inserting comprises an insertion mechanism affixed to the guide assembly, whereby actuation of the insertion mechanism inserts the instrument through the device.

BRIEF DESCRIPTION OF THE DRAWINGS

In the drawings, like reference characters generally refer to the same parts throughout the different views. Also, the drawings are not necessarily to scale, emphasis instead being placed upon illustrating principles of the present disclosure. The present disclosure, and exemplary embodiments according to the disclosure, are more particularly described in the following description, taken in conjunction with and in reference to the following drawings, in which.

DETAILED DESCRIPTION OF THE PREFERRED EMBODIMENTS

Figure 1:
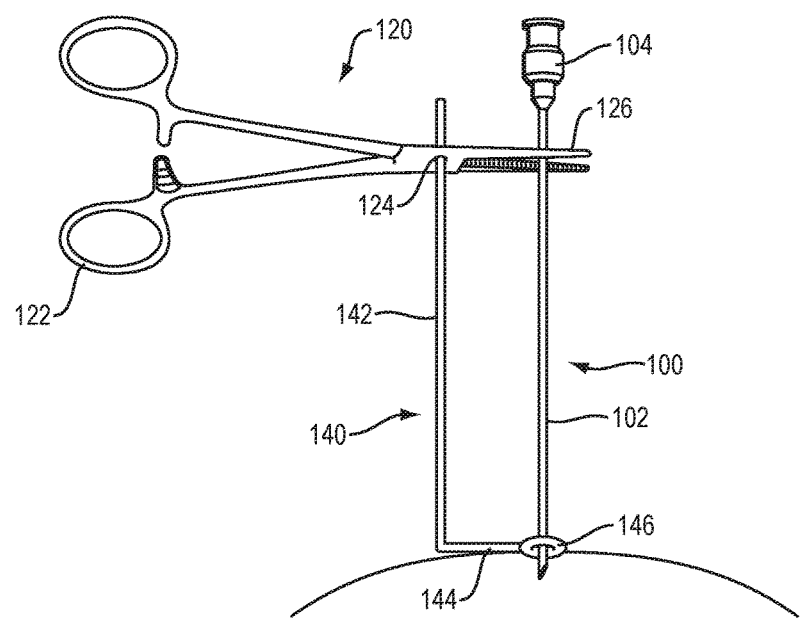
FIG. 1 illustrates a device having a guide assembly with an end effector and a handle in sliding relationship with a base component, in accordance with embodiments of the present disclosure.

Devices, systems and methods in accordance with the present disclosure are intended to save procedure time and improve targeting accuracy for instrument access by giving medical professionals stable and accurate guides to better orient and maintain alignment of an instrument during insertion along an insertion path, once a targeted point of entry and a targeted angle of insertion are determined.

An exemplary procedure that may benefit from devices of the present disclosure is antegrade needle access during a PCNL procedure, for example, according to the triangulation and bull's-eye targeting techniques described above, or variations on these techniques. Radiopaque material that is incorporated into the needle will appear as an image on a fluoroscopy display, while other materials such as plastics that are transparent to radiation and are not radiopaque do not appear on the display. Additionally, radiopaque contrast dyes can be injected into a body structure or tissue, such as a target calyx in a kidney, so that the structure or tissue can be visualized on the screen of the fluoroscope display.

In the embodiments of the present disclosure described herein, a typical use of radiopaque materials is in conjunction with a fluoroscope. However, other energy emitting devices similar to fluoroscopes may be suitable for use with devices and methods according to the present disclosure. Additionally, although some of the embodiments described herein may refer to only radiopaque materials for use as an imaging reference material, other types of imaging reference materials may be used in connection with other imaging systems (such as ultrasound, MRI or CAT-scan devices). If the materials used are changed from, for example, a metal to, for example, a fluid-filled or a gas-filled material with a known density, then such materials may be imaged with an MRI device or CAT-scan device. Alternatively, echogenic patterns could be applied to the surface of the instruments and/or devices in order to make them visible with an ultrasound probe.

Various embodiments of devices, systems and methods according to the present disclosure are described for guiding an instrument into a body of a patient, at a targeted point of entry and along an insertion path at a targeted insertion angle. The devices comprise a base component, a guide assembly, and optionally an insertion mechanism. In use, the base component aligns the instrument with the point of entry and the guide assembly cooperates with the base component to allow for the instrument to be aligned and fixed at a circumferential angle around an axis perpendicular to the point of entry and at a vertical angle away from the axis in a direction toward the body. In some embodiments, an insertion mechanism allows for the instrument, once it is aligned and fixed in position, to be mechanically inserted without a medical professional having to physically contact the instrument.

Imaging reference materials, such as radiopaque materials, may be incorporated into the material of the instruments and/or devices of the present disclosure, or coated or otherwise deposited thereon, so that either or both of the instrument and device may be aligned under fluoroscopy with the targeted entry point and targeted insertion angle, which have been determined by, for example, the targeting techniques described above. Once aligned, the angle and orientation of the instrument is maintained by the devices of the disclosure, and may be monitored and confirmed with fluoroscopy.

The instrument may be part of various systems of the disclosure, or may be supplied separately and introduced to the devices prior to or at the time of a procedure. As depicted throughout FIGS. 1-11B of the disclosure, in some embodiments, the instrument may be an access needle 100 with hollow tube 102 and sharp beveled tip at the distal end of the needle that is able to pierce tissue. In some embodiments, for example, in use in a PCNL procedure, a suitable diameter of the needle ranges from 14 to 21 gauge, and includes ranges therebetween, including preferably 16 to 18 gauge, in order to keep the insertion path narrow but at a diameter that can accommodate a guidewire. In some embodiments, the material of the needle may be surgical grade stainless steel, such as 306 stainless steel, an alloy of materials, such as Nitinol, or some other compatible material commonly known in the art to be suitable for surgical procedures. Any of the above materials may include a polymer coating, such as a PTFE coating. In some embodiments, an engagement hub 104 is included at the proximal end of the needle and may be configured to accommodate another device, for example, as the male or female portion of a threaded luer-lock. Such other devices may include a syringe in fluid communication with tube 102 for purposes of injecting or aspirating through hollow tube 102. Alternatively, such other device may be an integrated hub unit with guide assembly 1120 and base component 1140 according to the disclosure described further below with reference to FIG. 11A. It is also contemplated that in some embodiments the instrument may be solid rather than tubular. As described above, radiopaque substances may be incorporated as part of the material of the needle or may be coated or otherwise applied to the needle, at different points along the length of the needle. Alternatively, various other diameters, configurations and materials for instruments and devices according to the present disclosure may be chosen to accommodate the particular use contemplated for the instruments and the devices and procedures with which the instruments will be used.

FIGS. 1-11B illustrate exemplary embodiments of devices in accordance with the present disclosure that include a base component and guide assembly. The base component is configured to be oriented and fixed in a first position that corresponds to a targeted point of entry. The guide assembly has a first element cooperating with the base component to orient the instrument with respect to the first position. A second element of the guide assembly is configured to be oriented and fixed in a second position that corresponds to the targeted insertion angle. A third element of the guide assembly is configured to translate the insertion angle to the instrument as it guides the instrument along its longitudinal axis into the body. Wherever reference is made in the present disclosure to the first position or the second position of a device in accordance with the present disclosure, it is understood that the first position corresponds to the particular targeted point of entry for a device and the second position corresponds to the particular targeted insertion angle for the device.

FIG. 1 illustrates an exemplary embodiment of a device in accordance with the present disclosure in which guide assembly 120 is in sliding relationship with base component 140. Base component comprises a base rod 142 extending to a distal end and a leg 144. Leg 144 extends perpendicular from the distal end of base rod 142 to a terminal end. The distal surface of the leg provides for stable engagement of the device against the body during insertion. Although a single leg 144 is illustrated, any number of legs 144 may be suitable. Base rod 142 in conjunction with guide assembly 120 aligns the longitudinal axis of instrument 100 parallel to base rod 142 during insertion. In some embodiments, such as shown in FIG. 1, terminal end of leg 144 may include through-hole 146. Through-hole 146 has a diameter which slidingly engages and maintains instrument 100 at the first position (targeted point of entry). Other shapes and configurations at terminal end of leg 144 that perform the function of through-hole 146 are contemplated. Radiopaque material may be incorporated into or deposited onto through-hole 146, so as to provide a reference point under imaging with respect to instrument 100.

Guide assembly 120 comprises a modified Kelly clamp configuration with a shaft extending perpendicular to base rod 142. The first element of guide assembly 120 is end effector 126 at the distal end of the shaft. End effector 126 includes opposed clamping arms of the modified Kelly clamp, and is configured to reversibly engage and maintain instrument 100 at the first position during insertion. The third element of guide assembly 120 comprises guide component 124, at a middle portion of the shaft. Guide component 124 includes a through-lumen at the pivot axis of the arms of the modified Kelly clamp, and is configured to couple the shaft of guide assembly 120 in sliding relationship along base rod 142. The second element of guide assembly comprises handle 122 at a proximal end of the shaft. Handle 122 includes the thumb and finger grips of the modified Kelly clamp.

In use, handle 122 may be used by a medical professional to place the device at the targeted point of entry, with instrument 100 engaged between the clamping arms of end effector 126, parallel to base rod 142. Once the device with an instrument engaged is aligned and maintained by the medical professional at the targeted point of entry and insertion angle, handle 122 may be used to slide guide assembly along base 142, whereby instrument 100 is inserted into the patient's body with the longitudinal axis of instrument 100 following the axis of the base rod and the targeted angle of insertion.

Figure 2A:
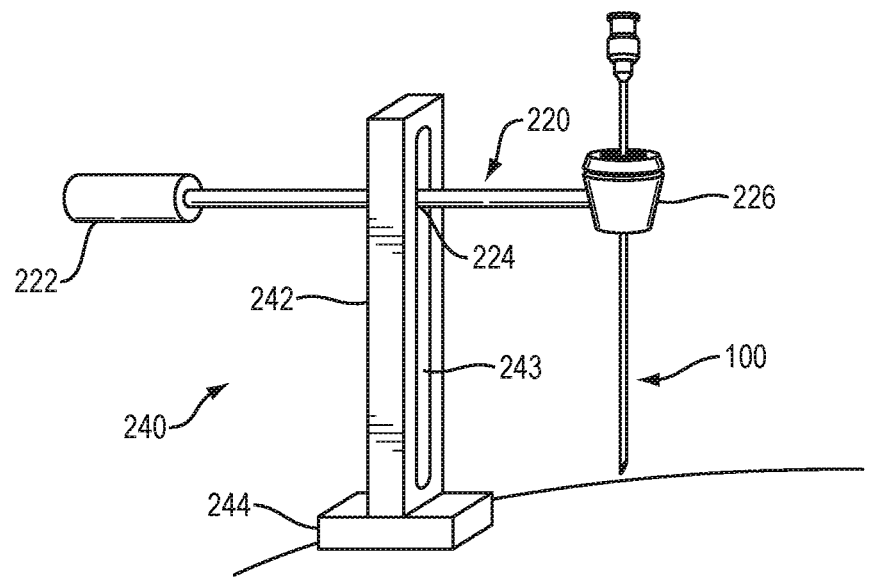
FIG. 2A illustrates a device having a guide assembly with an end effector and a handle in sliding relationship with a base component, in accordance with embodiments of the present disclosure.
Figure 2B:
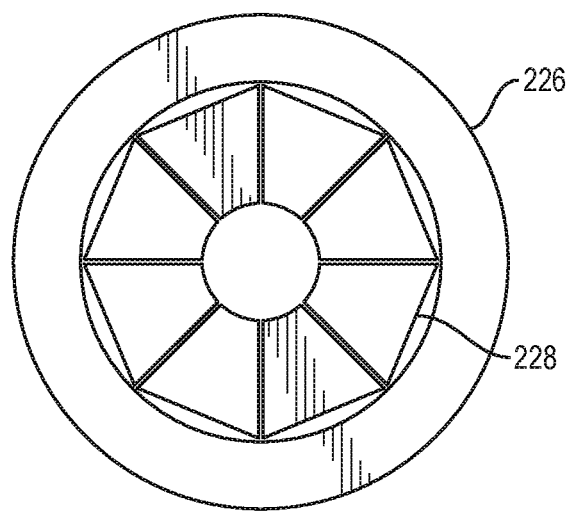
FIG. 2B illustrates a top view of an embodiment of an end effector, in accordance the device of FIG. 2A.

FIGS. 2A and 2B illustrate an exemplary embodiment of a device in accordance with the present disclosure, similar to that of FIG. 1, in which guide assembly 220 is in sliding relationship with base component 240. Base component comprises base rod 242 with guide slot 243 extending to a distal end and leg 244. Leg 244 extends perpendicular from each side of the distal end of base rod 242, with the distal surface of leg 244 providing for stable engagement of the device against the body during insertion. In some embodiments, the distal surface of legs 144 and 244, of FIG. 1 and FIG. 2A, respectively, may additionally include a tacky surface or adhesive to enhance the stable engagement of the device against the body. Although a pedestal configuration of leg 244 is illustrated with respect to FIG. 2A, any number and configuration of legs 244 which perform a similar function may be suitable. Base rod 242 in conjunction with guide assembly 220 aligns the longitudinal axis of instrument 100 parallel to base rod 242 during insertion.

Guide assembly 220 comprises a shaft extending perpendicular to base rod 242. The first element of guide assembly 220 is end effector 226, at the distal end of the shaft, which may comprise a collet mechanism, such as shown in FIG. 2A. The exemplary collet mechanism of FIG. 2A, as will be understood to those of skill in the art, includes an upper and lower portion that rotate with respect to each other. Fingers 228 are arranged around the periphery of the mechanism and define a through-lumen to accommodate instrument 100. The through-lumen may be reduced or increased in diameter to reversibly engage instrument 100 by rotating the upper and lower portions clockwise or counter-clockwise with respect to each other, similar to the function of a drill chuck used to engage and release a drill bit. The end effector 226 when engaged maintains instrument 100 at the first position during insertion. The third element of guide assembly 220 comprises guide component 224, at a middle portion of the shaft. Guide component 224 aligns the shaft of guide assembly 220 in sliding relationship along the guide slot 243 of base rod 242. The second element of guide assembly comprises handle 222 at a proximal end of the shaft. In use, handle 222 may be used by a medical professional to place the device at the targeted point of entry, with instrument 100 engaged by end effector 226 parallel to base rod 242.

Once the device with instrument 100 engaged is positioned and maintained by a medical professional at the point of entry and aligned with the targeted insertion angle, handle 222 may be used to slide guide assembly along guide slot 243, whereby instrument 100 is inserted into the patient's body with the longitudinal axis of instrument following the axis of the base rod and the targeted angle of insertion. With respect to the embodiments illustrated in FIGS. 1 and 2A-2B and other embodiment of the present disclosure, the configuration of the handle and end effector of the guide assembly and the configuration of the base component can be interchanged with each other, or substituted for various other mechanisms known to be suitable to perform the intended function.

Figure 3:
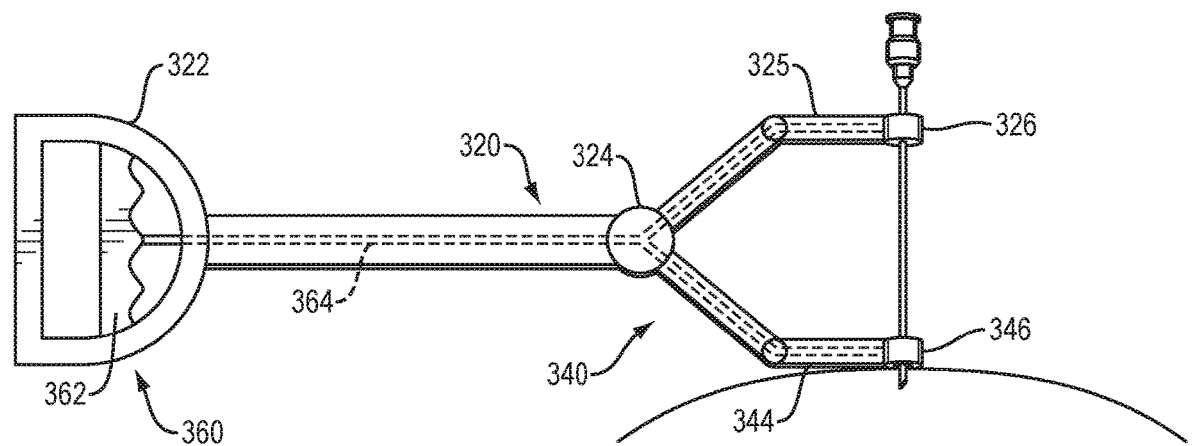
FIG. 3 illustrates a device having an integrated guide assembly and base component with a first arm and second arm in cooperative arrangement, and a handle with an insertion mechanism, in accordance with embodiments of the present disclosure.

FIG. 3 illustrates an exemplary embodiment of a device in accordance with the present disclosure, in which guide assembly 320 is integrated with base component 340 and comprises a shaft including first arm 325 at a distal end portion of the shaft. The first arm is in cooperative arrangement with second arm 344 of base component 340. The first element of guide assembly 320 is end effector 326 at the terminal end of first arm 325. The end effector may be configured in any suitable manner, for example utilizing the collet mechanism described above, so as to be able to reversibly engage instrument 100. The second arm 344 includes through-hole 346 at the terminal end, which is configured to slidingly engage instrument 100. Other shapes and configurations that perform the function of through-hole 346 are contemplated. The third element of guide assembly 320 is articulating component 324, located along a distal portion of the shaft and functioning as a pivot joint for the proximal end of the first and second arms where they join the shaft. The second element of guide assembly 320 is D-shaped handle 322 at the proximal end of the shaft.

In other embodiments, the handle may be configured in any shape that is suitable for grasping and manipulating the device. In use, handle 322 may be grasped by a medical professional to position and maintain the device at the first and second position with instrument 100 engaged by end effector 326. Second arm 344 functions in part to stabilize the device against the patient's body. First and second arms (325, 344) cooperate to align the longitudinal axis of instrument 100 perpendicular to the shaft when it is introduced to the device. Radiopaque material may be incorporated into or onto either or both of end effector 326 and through-hole 346 to aid in alignment of the instrument with the targeted insertion angle.

Once the device with instrument 100 engaged is aligned and maintained by the medical professional at the targeted point of entry and insertion angle, first arm 325 may be manipulated manually toward second arm 344, whereby instrument 100 is inserted into the patient's body. As arranged, the longitudinal axis of instrument 100 tracks the targeted angle of insertion along the axis line defined between end effector 326 and through-hole 346. Alternatively, in some embodiments, the device may include insertion mechanism 360 with actuation device 362. Device 362 is connected, via cable 364 or other suitable actuation means, in cooperative relationship with articulating component 324 and first and second arms (325, 344), such that retracting actuation device 362 proximally causes first arm 325 to move toward second arm 344 inserting instrument 100.

Figure 4:
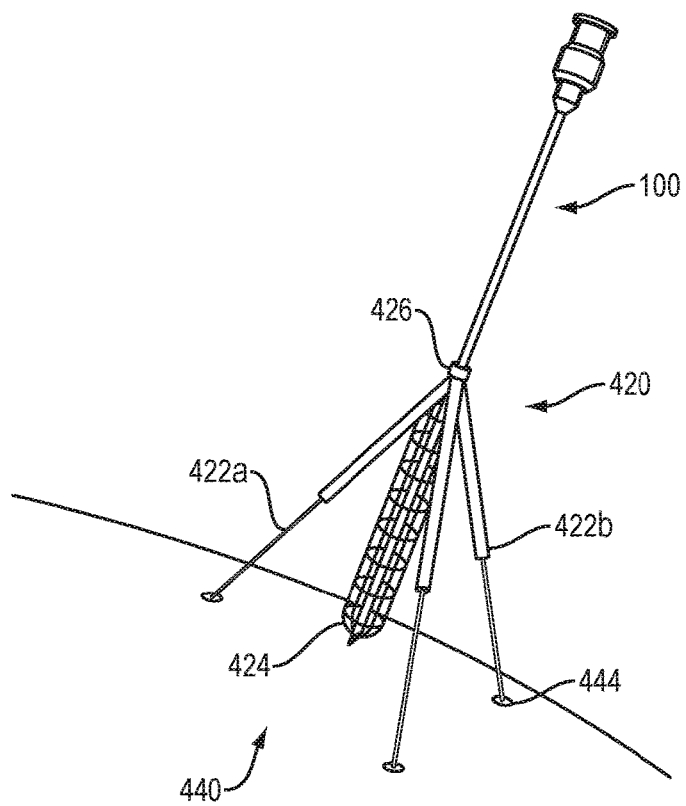
FIG. 4 illustrates a device having an integrated guide assembly and base component with adjustable length legs, collar and cage alignment device, in accordance with embodiments of the present disclosure.
Figure 5:
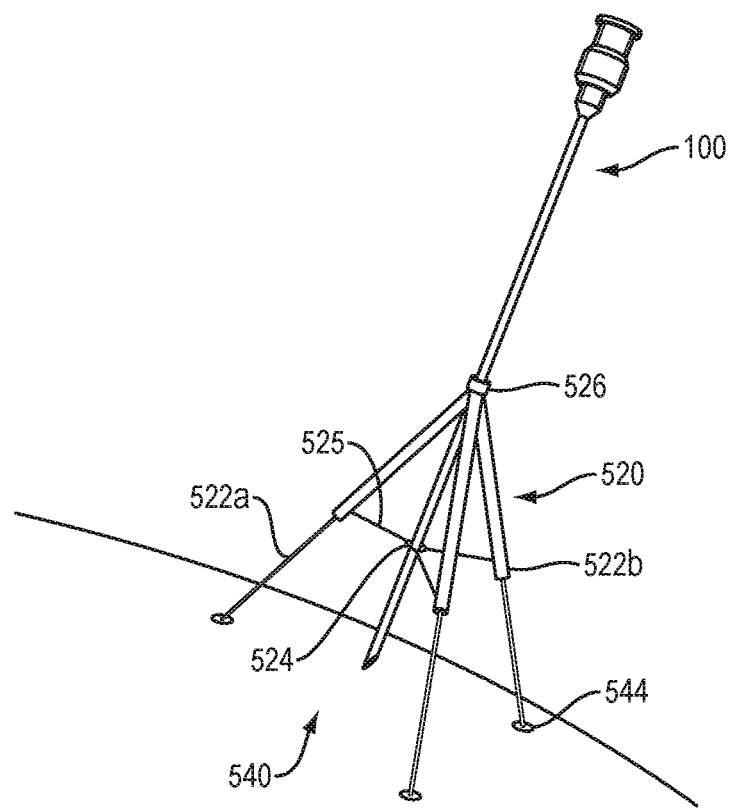
FIG. 5 illustrates a device, similar in configuration to the device of FIG. 4, with a collar alignment device, in accordance with embodiments of the present disclosure.

FIGS. 4-5 illustrate exemplary embodiments of a device in accordance with the present disclosure, in which guide assemblies (420, 520) are integrated with respective base components (440, 540). The guide assembly in each of the embodiments comprises three or more legs (422b, 522b) having a distal end and a proximal end, each leg having one or more feet (444, 544) as part of the base component (440, 540), extending radially from the distal end of the legs. The feet provide stable engagement of the device against the patient's body during insertion of instrument 100, and may include a tacky surface or adhesive on the bottom to aid in stabilizing the device.

The first element of the guide assembly is collar (426, 526) which joins the proximal ends of the legs together and includes a through-hole to slidingly accommodate instrument 100 therethrough when instrument 100 is introduced to the device. Alternatively, collar (426, 526) may include a component that allows it to reversibly engage instrument 100 (e.g., a threaded or grooved surface on the interior surface of the collar that is sized to engage a corresponding groove or thread on the inside of the luer-lock hub fitting of the instrument). Each of legs (422b, 522b) include leg portions (422a, 522a) that are adjustable in length as the second element of the guide assembly. As shown in FIGS. 4-5, in some embodiments, the adjustable leg portions (422a, 522a) may be telescoping extensions that are coaxial with legs (422b, 522b). Each portion is capable of independent adjustment by sliding up and into the respective leg with which it is associated and then locked or otherwise maintained in position so as to align device with the targeted insertion angle. Various mechanisms for maintaining position of the adjustable portions once the desired length is achieved, for example, pneumatic pressure, friction, twist and lock, ratchet, clip-on, or pin and hole arrangements, are contemplated. The third element of guide assembly (420, 520) is alignment device (424, 524) which functions in cooperation with collar (426, 526) to align the longitudinal axis of instrument 100 with the targeted entry point and insertion angle once the device is set to the corresponding first and second position and instrument 100 is introduced to the device. Radiopaque material may be incorporated within or disposed onto either or both of collar (426, 526) and alignment device (424, 524) to aid in aligning the device with the targeted insertion angle and maintaining that position for instrument 100 during insertion.

As shown for example in FIG. 4, alignment device 424 may be a cage element aligned with and extending longitudinally from collar 426. In other embodiments, for example as shown in FIG. 5, alignment device may be a second collar 524 arranged in the middle of legs 522b and aligned longitudinally with collar 526 at the proximal end of the legs portions 522a. Spans 525 extend from and connect second collar 524 to legs 522b. In use, the device is aligned with the targeted entry point and the length of the legs is adjusted under imaging to the second position at the targeted insertion angle. The legs may then be locked in place and instrument 100 inserted into the patient's body with the longitudinal axis of the instrument following the axis defined by the line between the collar and the alignment device of the guide assembly.

Figure 6A:
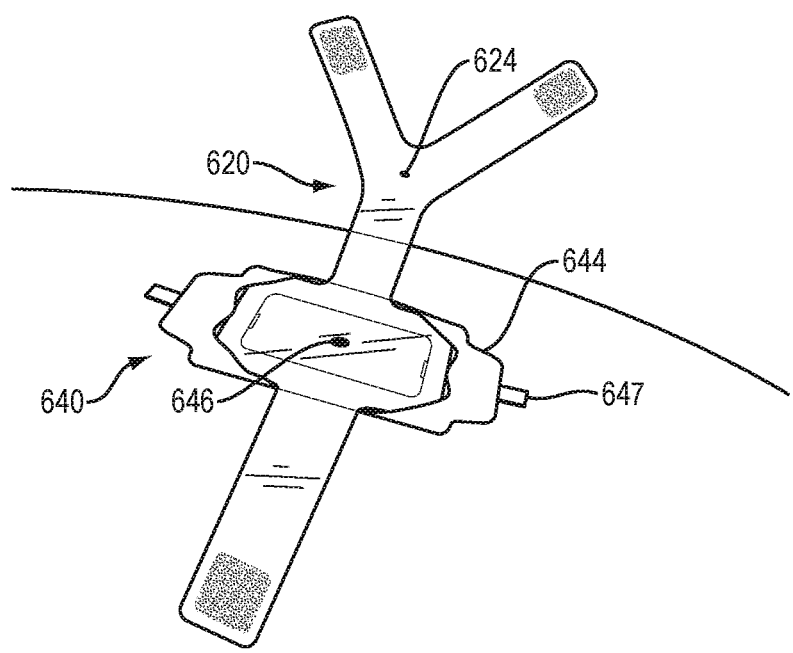
FIG. 6A illustrates a device having a base component and removably engageable guide assembly with alignable lumen and guide holes, in accordance with embodiments of the present disclosure.
Figure 6B:
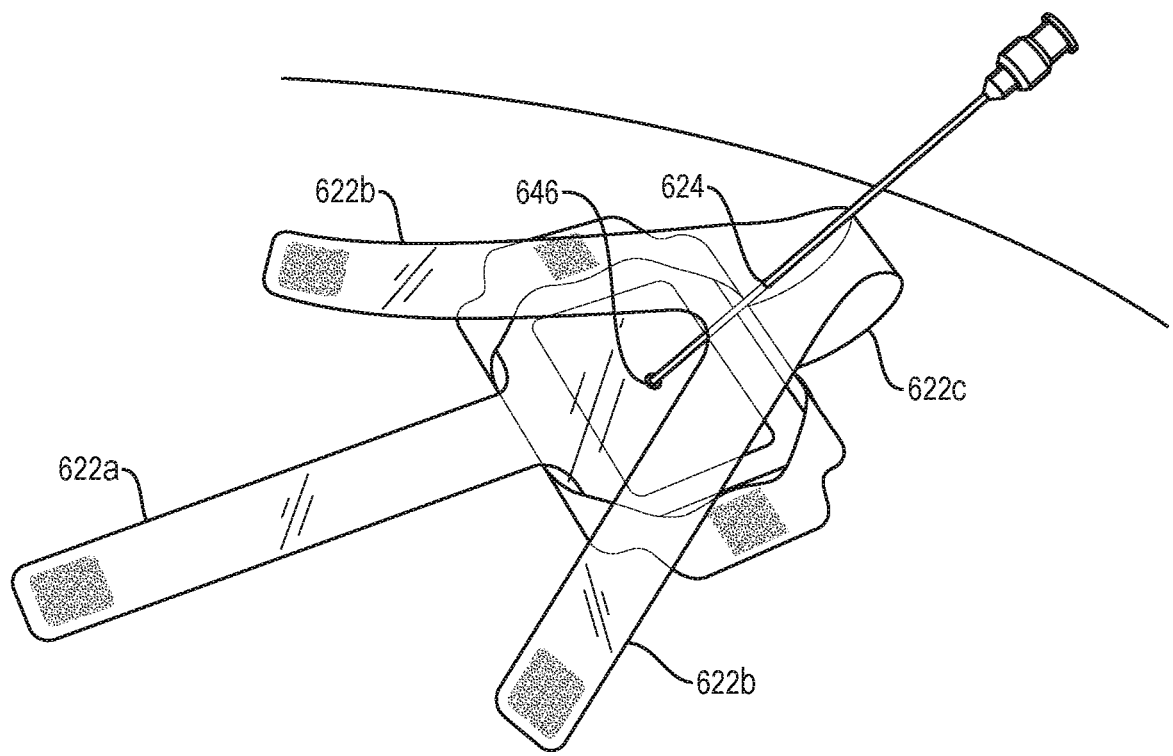
FIG. 6B illustrates the device of FIG. 6A with the guide holes of the guide assembly aligned with the lumen of the base component, in accordance with embodiments of the present disclosure.

FIGS. 6A and 6B illustrate an exemplary embodiment of a device in accordance with the present disclosure in which guide assembly 620 is removably engageable with the proximal surface of base component 640. The base component has a distal surface 644 that may be contoured and may include an adhesive in order for the base component to conform to the body of a patient and provide stable engagement of the device against the body during insertion of instrument 100. A lumen 646 extending through the base component is aligned in the first position at the targeted point of entry prior to and during insertion.

The first element of guide assembly 620 is a first guide hole 626 that is aligned with lumen 646 of base component 640 when the guide assembly is engaged with the base component. In some embodiments, for example as shown in FIG. 6A, guide hole 626 may be a window in the guide assembly that is broadly aligned with lumen 646. In other embodiments, guide hole 626 may be similar in diameter to and narrowly aligned with lumen 646. The third element of guide assembly 620 is a second guide hole 624 that is configured to slidingly accommodate instrument 100 in alignment with guide hole 626 of the guide assembly and lumen 646 of the base component during insertion. The second element of guide assembly 620 comprises first guide 626, second guide hole 624 and a mechanism 622 to adjust and fix the second guide hole relative to the first guide hole in the second position corresponding to the targeted insertion angle.

In the embodiments illustrated in FIGS. 6A and 6B, mechanism 622 of the guide assembly is a flexible plastic member including a longer arm portion 622a and shorter arm portions 622b in a Y-shaped configuration. A middle of the longer arm portion includes a window, as first guide hole 626, which is removably engageable with base component 640. Once lumen 646 is aligned with the targeted entry point or first position, tabs 647 may be removed to reveal adhesive that secures base component 640 in place on the patient. Adhesive at the end of the terminal end of the longer arm portion 622a may be used secure that end to the patient as well. Guide assembly is engaged under corner edges of base component 640, which also functions to align window 626 with lumen 646.

In use, shorter arm portions 622b including second guide hole 624 are bent back over the window, and attached to the patient's body, for example with adhesive as shown, at the ends of shorter arm portions 622b. The position of the shorter arm portions is adjusted before adhering the arms to the patient in order to align the second guide hole relative to the first guide hole and lumen, in the second position corresponding to targeted insertion angle. If the angle is incorrect, the shorter arm portions may be used to reposition the second guide hole and then secured again to the patient.

This arrangement aligns the longitudinal axis of instrument 100 with the targeted entry point and insertion angle, once the device is set to the corresponding first and second position and instrument 100 is introduced to the device. Radiopaque material may be incorporated on any or all of first and second guide holes (626, 624) and lumen 646 to aid in alignment of the device under imaging to the insertion angle and maintaining that position for the instrument during insertion.

Figure 7:
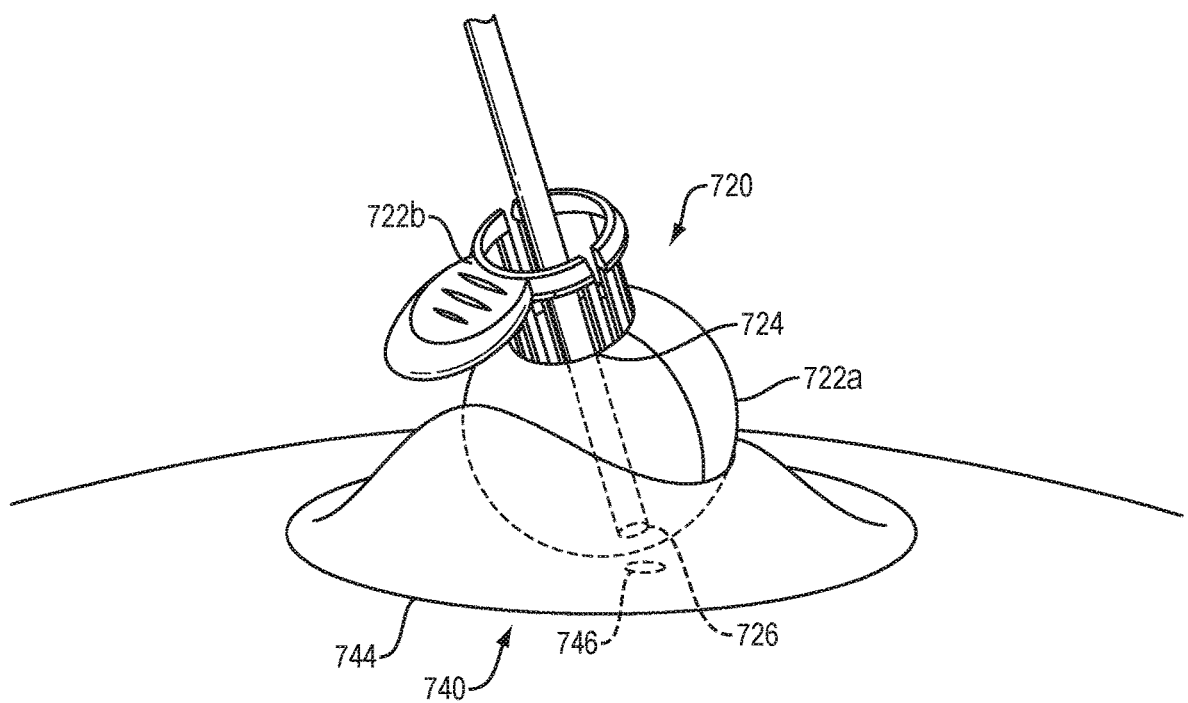
FIG. 7 illustrates a device having a guide assembly and base component in a ball and socket arrangement with alignable lumen and guide holes and a push tab mechanism, in accordance with embodiments of the present disclosure.

FIG. 7 illustrates an exemplary embodiment of a device in accordance with the present disclosure, in which guide assembly 720 is engaged with the proximal surface of base component 740 in a ball and socket arrangement. The base component has a distal surface 744 that may be contoured and may include an adhesive in order for the base component to conform to the body of a patient and provide stable engagement of the device against the body during insertion of instrument 100. A lumen 746 extending through the base component is aligned in the first position at the targeted point of entry prior to and during insertion.

The first element of guide assembly 720 is a first guide hole 726 that is aligned with lumen 746 of base component 740 when the guide assembly is engaged with the base component. The third element of guide assembly 720 is a second guide hole 724 that is configured to slidingly accommodate instrument 100 in alignment with guide hole 726 of the guide assembly and lumen 746 of the base component during insertion. The second element of guide assembly 720 is ball 722a seated in a socket formed in the proximal surface of base component 740. The ball 722a includes first guide hole 726 and second guide hole 724 in linear alignment. Together they form a through lumen in ball 722a in alignment with lumen 746 of the base component. The ball is rotatable in the socket to align the through lumen to the second position corresponding to the targeted insertion angle.

A moveable mechanism 722b is configured to frictionally fix the ball to the second position. In some embodiments, for example as shown in FIG. 7, mechanism 722b is a two-piece push tab that when pushed into ball 722a is configured to frictionally fix the ball at the second position. This arrangement aligns the longitudinal axis of instrument 100 with the targeted entry point and insertion angle, once the device is set to the corresponding first and second position and instrument 100 is introduced to the device. Radiopaque material may be incorporated on any or all of first and second guide holes (726, 724) and lumen 746 to aid in alignment of the device under imaging to the insertion angle and maintaining that position for the instrument during insertion.

Figure 8A:
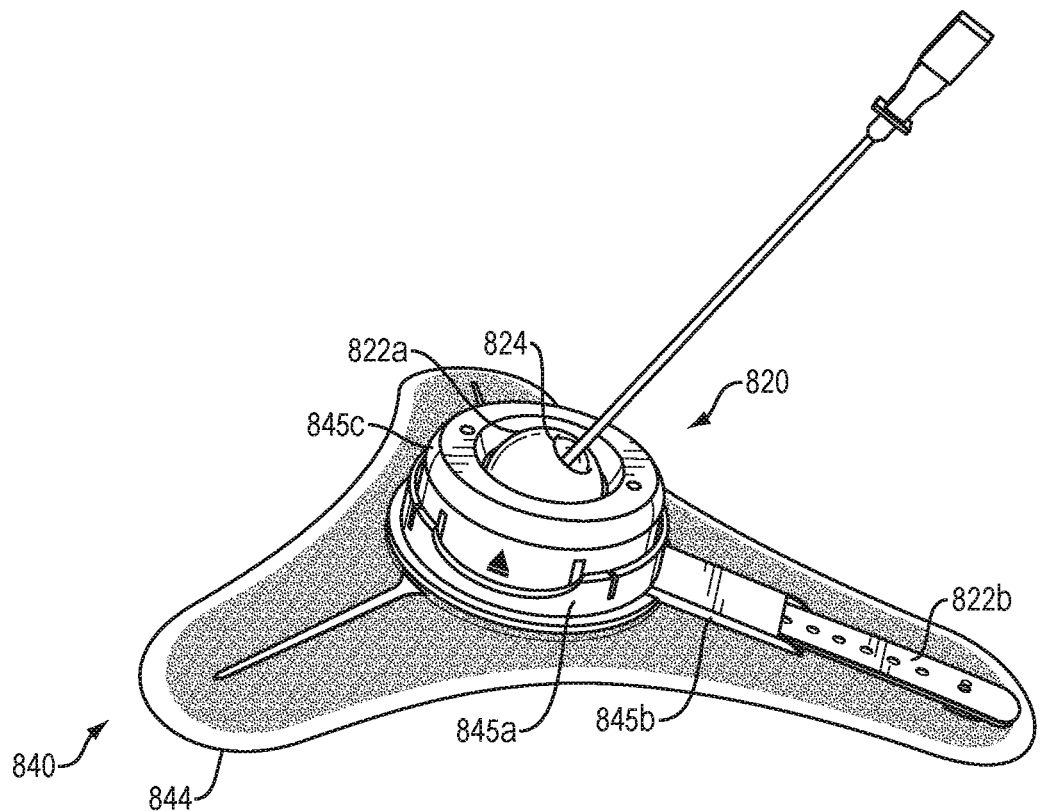
FIG. 8A illustrates a device having a guide assembly and base component in a ball and socket arrangement with alignable lumen and guide holes and a pull tab mechanism, in accordance with embodiments of the present disclosure.
Figure 8B:
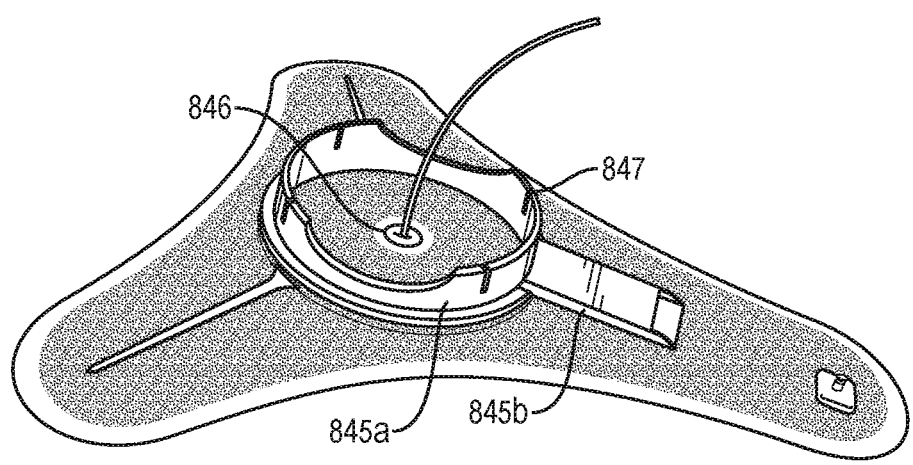
FIG. 8B illustrates the device of FIG. 8A with the guide assembly and a portion of the base component removed from the remainder of the base component, in accordance with embodiments of the present disclosure.

FIGS. 8A and 8B, illustrate an exemplary embodiment of a device in accordance with the present disclosure, similar to that of FIG. 7, in which guide assembly 820 is engaged with the proximal surface of base component 840 in a ball and socket arrangement. Base component 840 comprises stationary housing portion 845a and pull tab housing portion 845b. The distal surface 844 may be contoured and may include an adhesive in order for stationary housing portion 845a to conform to the body of a patient and provide stable engagement of the device against the body during insertion of instrument 100. A lumen 846 extends through the stationary housing portion 845 and is aligned in the first position at the targeted point of entry prior to and during insertion. Base component 840 also includes removable housing portion 845c with a proximal surface that forms the socket for the guide assembly.

The first element of guide assembly 820 is a first guide hole that is in fixed alignment with lumen 846 of base component 840. The third element of guide assembly 820 is a second guide hole 824 that is configured to slidingly accommodate instrument 100 in alignment with guide hole of the guide assembly and lumen 846 of the base component during insertion. The second element of guide assembly 820 is ball 822a seated in the socket of removable housing portion 845c. The ball 822a includes first guide hole and second guide hole 824 in linear alignment, and together form a through lumen in ball 822a in alignment with the lumen of the base component. The ball is rotatable in the socket to align the through lumen to the second position corresponding to the targeted insertion angle.

A moveable mechanism 822b is configured to frictionally fix the ball to the second position. In some embodiments, for example, as shown in FIG. 8A, mechanism 822b is a pull tab recessed within pull tab housing portion 845b. Tab 822b is configured with ball 822a such that pulling tab 882b radially away from ball 822a frictionally fixes the ball to the second position. This arrangement aligns the longitudinal axis of instrument 100 with the targeted entry point and insertion angle, once the device is set to the corresponding first and second position and instrument 100 is introduced to the device. Radiopaque material may be incorporated within or disposed upon any or all of the first guide hole and the second guide holes (824) and lumen 846 to aid in aligning the device under imaging to the insertion angle and maintaining that position for the instrument during insertion.

In some embodiments, for example as shown in FIG. 8B, after instrument 100 is inserted into a patient's body, a guidewire is placed through instrument 100 and the instrument is then removed. Removable housing portion 845c may then be separated along with ball 822a and pull tab 822b from stationary housing portion 845a and removed from the patient over the guidewire. The stationary housing portion 845a, may remain behind and slots 847 may act as stationary anchors for other medical devices, such as guidewires, used in the procedure.

Figure 9:
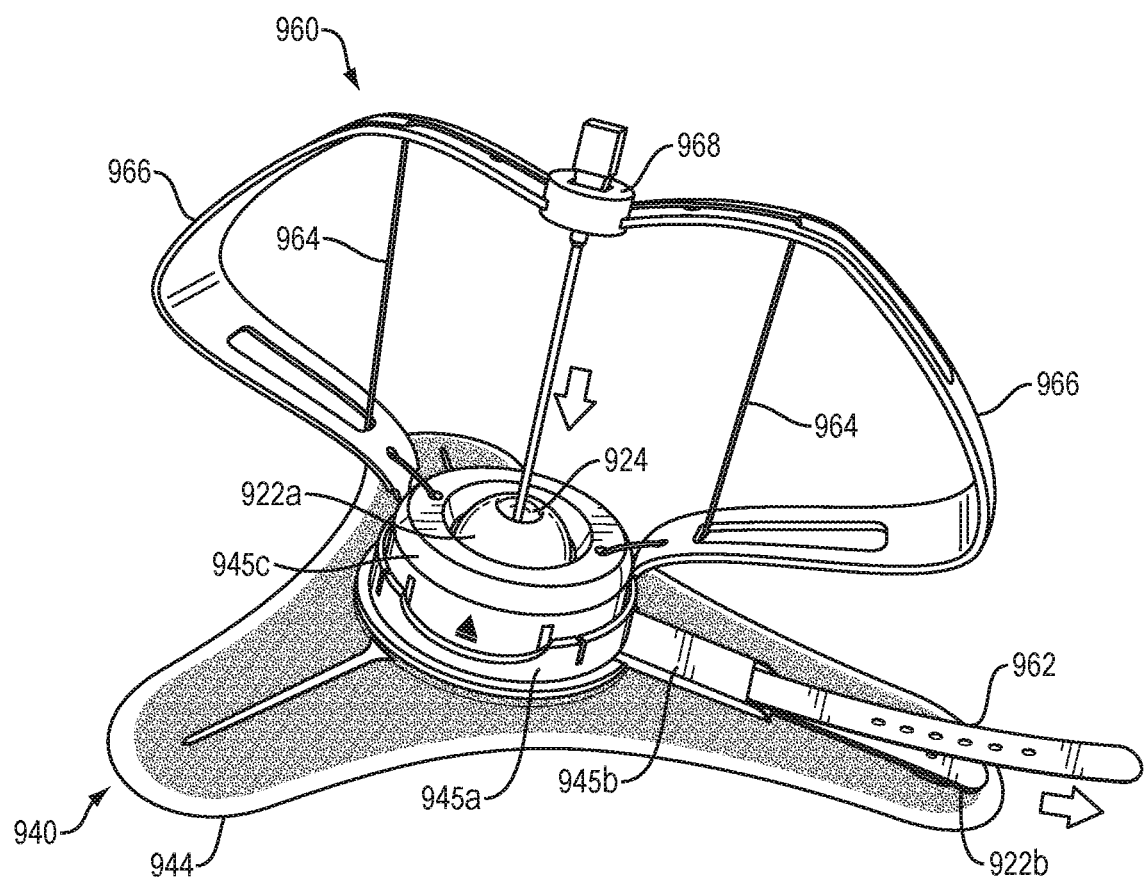
FIG. 9 illustrates a device having a guide assembly and base component in a ball and socket arrangement with alignable lumen and guide holes, pull tab mechanism and insertion mechanism, in accordance with embodiments of the present disclosure.

FIG. 9 illustrates an exemplary embodiment of a device in accordance with the present disclosure, in which guide assembly 920 and base component 940 have the ball and socket arrangement of the exemplary embodiment of FIGS. 8A and 8B, and insertion mechanism 960 is affixed to the guide assembly. Base component 940 comprises stationary housing portion 945a, pull tab housing portion 945b, removable housing portion 945c and lumen 946 extending through the stationary housing portion 945a. Guide assembly 920 has first guide hole 926, second guide hole 924, and ball 922a seated in the socket of removable housing portion 945c.

The ball may be rotated in the socket to align the through lumen to the second position corresponding to the targeted insertion angle, and secured with pull tab 922b recessed within pull tab housing portion 945b. Radiopaque material may be incorporated within or on any or all of first and second guide holes (926, 924) and lumen 946 to aid in aligning the device under imaging to the insertion angle and maintaining that position for instrument 100 during insertion.

In some embodiments, an insertion mechanism 960, for example as illustrated in FIG. 9, is affixed to the sides of guide assembly 920 and includes instrument holder 968, flexible wing portions 966, insertion member 964 and insertion pull tab 962 in operable arrangement with each other. Wing portions 966 extend at one end from the side of guide assembly 920 to another end fixed at sides of instrument holder 968. Insertion member 964 is connected to insertion pull tab 962, and extends up, through and around removable housing portion 945c, wing portions 966 and instrument holder 968.

Insertion member 964 can comprises a single thread of material or multiple threads. Both ends of a single thread may be connected to pull tab 962, or only a single end thereof. Both ends of multiple threads of member 964 may be connected to pull tab 962, or only a single end thereof. A single thread may extent past instrument holder 968, or ends of multiple threads may be connected to each side of instrument holder 968 and threaded through the device to tab 962. In some embodiments, member 964 is a suture, wire or other material and may be wire, polymer or composed other material, suitable to perform the intended function.

In use, when instrument 100 is introduced and engaged in holder 968, and the ball has been fixed to the second position aligned with the insertion angle, pulling pull tab 962 radially away from guide assembly 920, results in a downward pulling force by insertion member 964 on wing portions 966. This force causes the wing portions to flex and moves the instrument holder with engaged instrument 100 toward the base component and guide assembly, in alignment with the first and second positions.

In some embodiments, for example as illustrated FIG. 8B, after instrument 100 is inserted into a patient's body, a guidewire is placed through instrument 100 and the instrument is then removed. Removable housing portion 945c may then be separated along with ball 922a and pull tab 922b from stationary housing portion 945a. In embodiments such as FIG. 9, removable housing portion 945c, when separated, removes insertion mechanism attached thereto as well.

Figure 10:
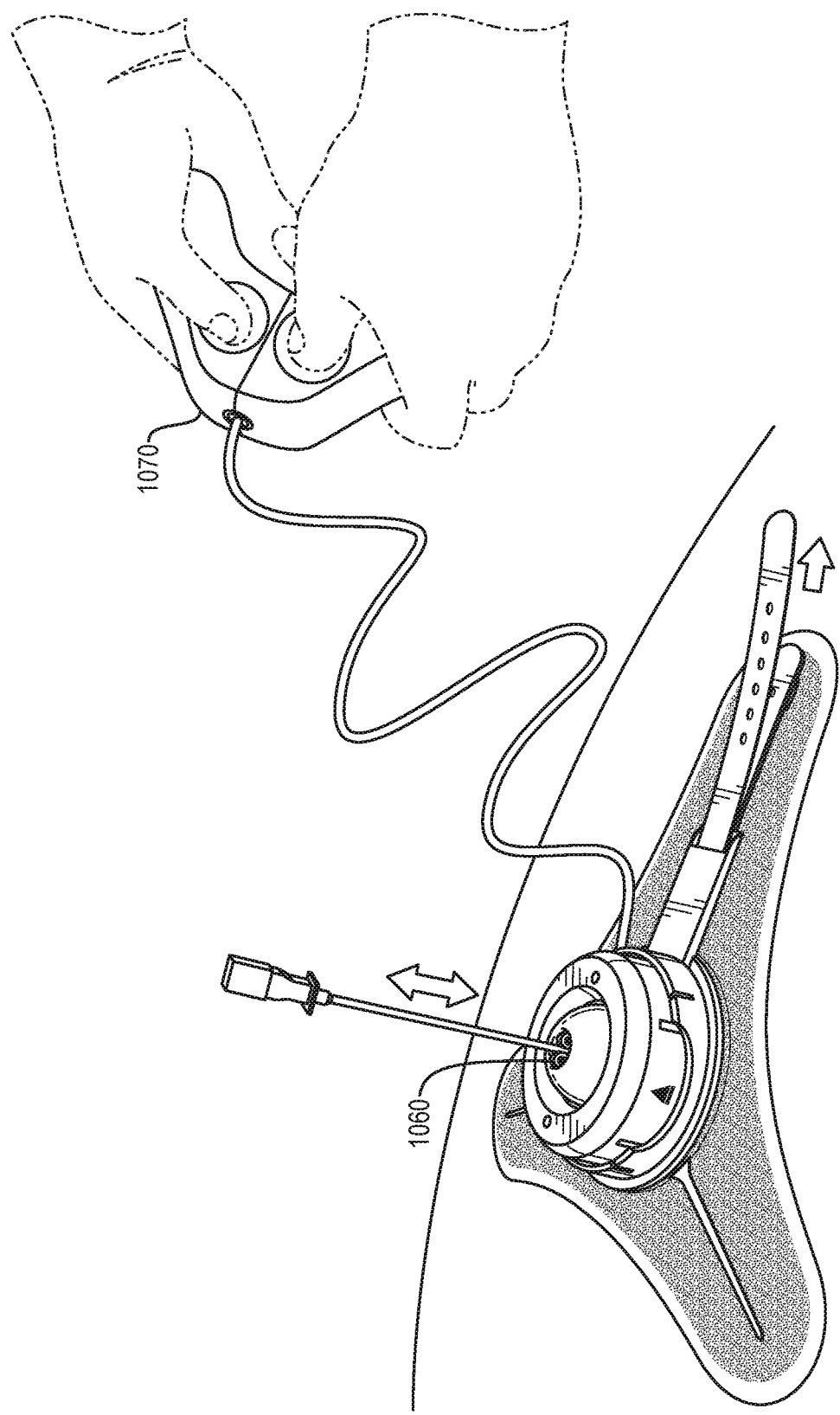
FIG. 10 illustrates a device having a guide assembly and base component in a ball and socket arrangement with a remote device for control of alignable lumen and guide holes and an insertion mechanism, in accordance with embodiments of the present disclosure.

FIG. 10 illustrates an exemplary embodiment of a device in accordance with the present disclosure, for example in accordance with any of the embodiments illustrated with reference to FIGS. 7-9, in which a remote control device is configured with a guide assembly and base component, such that the ball of the guide assembly can be oriented remotely within the socket of the base component. After the ball is fixed at the second position, insertion mechanism 1060 may be remotely operated to insert instrument 100 into the patient's body with the longitudinal axis of instrument 100 following the axis defined by the line between the first and second guide holes of the ball and the lumen of the base component. In some embodiments, for example as shown in FIG. 10, insertion mechanism 1060 may include opposing rollers configured within the profile of the ball above the first guide hole. The rollers function to frictionally engage the profile of instrument 100 when an instrument is introduced to the device. A motorized mechanism rotates the rollers in response to a signal from the remote control device, which in turn inserts or retracts the instrument held between the rollers. In other embodiments, various other shapes, configurations and materials for the insertion mechanism suitable to perform the intended function are contemplated.

Figures 11A, 11B:
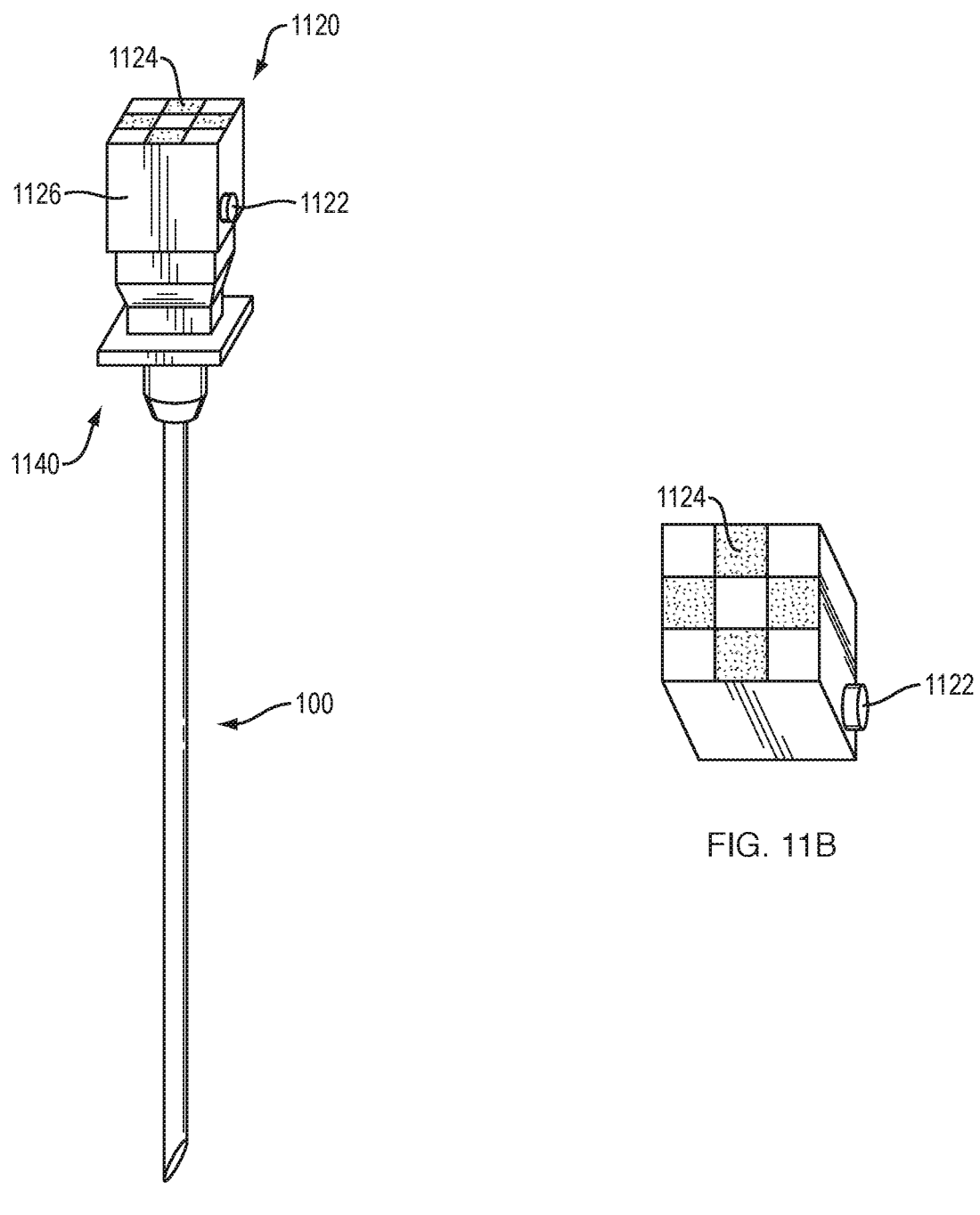
FIG. 11A illustrates a device having an integrated guide assembly and base component removably engageable with an instrument, electronic sensing position sensing mechanism and visual display, in accordance with embodiments of the present disclosure.
FIG. 11B illustrates a top view of the device of FIG. 11A with the integrated guide assembly and base component removed from the instrument, in accordance with embodiments of the present disclosure.

FIGS. 11A and 11B illustrate an exemplary embodiment of a device in accordance with the present disclosure in which guide assembly 1120 and base component 1140 are an integrated hub. The hub includes an element that is removably engageable with the proximal end of instrument 100. As shown in FIG. 11A, the first element of the guide assembly is the exterior surface 1126 of the hub, which may be grasped in use by a medical professional in order to align the hub and instrument 100 to the targeted entry point at the first position and maintain the hub and instrument aligned to the targeted insertion angle at the second position prior to and during insertion of instrument 100. Various shapes, configurations and materials for the hub, its exterior surface and the element engageable with the instrument, which are suitable to perform the intended functions are contemplated.

The second element of guide assembly 1120 is an electronic position sensing mechanism and connected set button 1122, the sensing mechanism being internal to the hub and the set button being configured on the surface 1126 of the hub. The arrangement and electronics of the sensing mechanism are configured to be reversibly set to the second position, such that when instrument 100 and hub are aligned to a targeted insertion angle, the set button may be activated, which sends a signal to the sensing mechanism to fix on the second position. Various embodiments of sensing mechanisms, such as accelerometers, gyroscopes, or magnetometers that are commonly used in motion tracking, guidance and positioning applications, and configurations and arrangement of set buttons, which are suitable to perform the intended function of acquiring and fixing on the second position are contemplated.

The third element of guide assembly 1120 is visual display 1124. In some embodiments, for example as shown in the top view of FIG. 11B, display 1124 may be an LED array set in a pattern of squares around a center square, the center square having a color that lights up (e.g., green), as long as the second position of the hub and instrument 100 are maintained by a medical professional in substantial alignment with the targeted insertion angle that mechanism 1122 has been fixed on. The squares surrounding the center square have a color that lights up (e.g., red), if the second position of the hub and instrument 100 are allowed to fall out of substantial alignment with the targeted insertion angle. Which red square lights up provides an indication of which way the instrument has to be oriented in order to correct alignment back to the targeted insertion angle. In some embodiments, an audible alert may be substituted for or used to complement the visual display. Various other configurations and patterns for the display which are suitable to perform the intended alert and correction function are contemplated.

Systems according to the present disclosure include devices for guided insertion of an instrument as described with reference to the exemplary embodiments above, in combination with an instrument to be inserted. As described above, in some embodiments, the instrument may be an access needle 100 with hollow tube 102 and a distal end that may have a sharp beveled tip that is able to pierce tissue. An engagement hub 104 at the proximal end of the needle may be configured to accommodate another device, for example, as the male or female portion of a threaded luer lock. Such other devices may include a syringe in fluid communication with tube 102 for purposes of injecting or aspirating through hollow tube 102. In some embodiments, the instrument may be single use and disposed of after the procedure in which it is inserted into a patient's body, while the whole of the device or a component of the guide assembly or base component of the device may be single use or reusable, if made with material that may be being properly sterilized. Devices for use with systems of the present disclosure may be according to any of the embodiments described above with reference to FIGS. 1-11B.

Various locating and positioning systems may be used to establish and maintain the targeted insertion point and targeted angle of insertion for an instrument as an alternative or in addition to the triangulation techniques described above. Such examples of locating and positioning systems include electromagnetic and optical systems. Optical systems may entail optical markers or beacons placed along the instrument and/or the guide assembly that are detectable by sensors, for example, external cameras fixed in position. By aiming the sensors at the beacon the distance and angle between them can be measured. For electromagnetic tracking, a sensor is used that creates an electromagnetic field across the location of interest and small coils or the like that are placed in or on the instrument and/or guide assembly are read by a computer processor. In both cases, the instrument position data must be matched to imaging data, so that the targeted angle of insertion may be calculated. Visual or auditory alerts may be associated with the beacon so that misalignment with the angle of insertion can be corrected during insertion of the instrument.

Such mechanisms may also include triangulation systems using ultrasonic transducers placed in each of three triangle positions of the base component, such as the exemplary base components illustrated in FIGS. 6A-10. The transducers sense targets along the instrument and/or guide assembly to echo locate the instrument position and angle of insertion. Such a system may produce a virtual image on a screen and superimpose the instrument position based upon the triangulation data received from the transducers. The medical professional can manipulate the instrument and/or guide assembly of the device in order to intersect the target location and fix the location or angle of insertion at the second position. The technology may be capable of sensing where the instrument is in real time, predicting the target location in real time (including predicting target motions, e.g., breathing) and then calculating and informing the user of the necessary motions to remove the error or difference between the current instrument position and the target location (i.e., to maintain the targeted angle of insertion such that the instrument continues to intersect the target when inserted).

Inertial position and locating is a self-contained technique in which measurements provided by accelerometers and gyroscopes are used to track the position and orientation of the instrument relative to a known starting point and orientation. By processing signals from these devices it is possible to track the position and orientation of the instrument. Inertial locating/positioning systems, for example, the sensing mechanisms described with reference to the exemplary embodiment depicted in FIGS. 11A-11B, include at least a computer processor and a platform or module containing accelerometers, gyroscopes, or other motion-sensing devices. The instrument is initially provided with its position (the targeted insertion angle) from another source (the medical professional), and thereafter computes its own updated position by integrating information received from the motion sensors. An advantage of this type of mechanism is that it requires no external references in order to determine its position or orientation once it has been initialized.

These examples of suitable locating and positioning systems may be used alone or in combination to establish and maintain the targeted insertion point and angle for an instrument prior to or in conjunction with insertion of the instrument in accordance with the guide devices and systems disclosed herein. Additional or alternative locating and positioning systems suitable for such uses are described in U.S. patent application Ser. No. 62/276,567, filed on Jan. 8, 2016, entitled "SURGICAL GUIDANCE DEVICES, SYSTEMS, AND METHODS" and assigned to Boston Scientific Corporation, the entire disclosure of which is incorporated herein by reference. These systems may be completely automated with various embodiments of guide device and systems, such as with respect to FIG. 10 to orient the ball of the guide assembly within the socket of the base component, in order to manipulate and maintain the insertion angle of the instrument with respect to the patient.

Various methods may be utilized in practice with devices and systems according to any of the embodiments described above with reference to FIGS. 1-11B and any other embodiments of the present disclosure. In the context of a PCNL procedure, for example, a targeted point of entry on the body and angle of insertion is determined with fluoroscopic imaging, a device according to an embodiment of the present disclosure, with an access needle and stylet as the instrument engaged by the device, is aligned to a first position at the targeted point of entry, the longitudinal axis of the needle and device are oriented to a second position corresponding to the targeted angle of insertion and in liner alignment with the first position. The bull's eye targeting technique is utilized with radiopaque markers on ends of the needle and/or ends of the device to confirm and fix linear alignment of the device and needle to the second position, after which the needle is inserted under fluoroscopy imaging guidance along the insertion path until the needle and stylet enter the target calyx of the kidney.

The stylet is removed from the needle and the proper depth of insertion and access to the target calyx is confirmed with imaging, visual confirmation of urine coming through the needle, aspiration of urine through a syringe connected to the needle, or some combination of the above. A guidewire is inserted through the needle and the needle is removed over the guidewire. The guidewire is left to guide instruments necessary to the PCNL procedure into the target calyx, such as dilating catheters, access sheaths, lithotripsy devices, retrieval devices and the like.

In some embodiments, the instrument may be removed from the patient's body together with the guide assembly and base component of the device. In other embodiments, the instrument may be removed before any component of the device, the device may be removed before the instrument, the instrument and guide assembly may be removed before the base component, or the instrument, guide assembly and portion of the base component may be removed before the remainder of the base component.

In some embodiments, for example, with reference to FIGS. 1-3 and FIGS. 11A-11B, the device is maintained at the first position manually by a medical professional holding the device in place, with reference to FIGS. 4-5, the legs of the guide assembly and base component feet maintain the first position, and with reference to FIGS. 6A-10, a tacky or adhesive surface maintains the first position. In some embodiments, for example with reference respectively to FIGS. 1-3, and 11; FIGS. 4-5; and FIGS. 6A-10, respectively, the device is oriented and fixed to the second position by manually holding the position, by locking adjustable legs of the guide assembly, or by fixing rotation of a ball of the guide assembly with respect to the socket of the base component. In some embodiments, the instrument may be engaged with the device prior to aligning the device in the first position, prior to orienting the device in the second position but after the first position, or after the device is aligned to the first position and oriented and fixed to the second position.

In methods according to some embodiments of the present disclosure, the step of orienting the second element, in linear alignment with the first element, to a second position may be as described above at any circumferential angle ranging from 0 to 360 degrees around an axis perpendicular to the first position and at any vertical angle ranging from 0 to 45 degrees away from such axis in a direction toward the body.

In some embodiments of the various methods, the step of inserting may comprise an insertion mechanism such as those insertion mechanisms described above, integrated with or affixed to the guide assembly, whereby actuation of the insertion mechanism inserts the instrument through the device without the instrument having to be handled by the medical professional.

The devices according to the embodiments described and according to other embodiments of the present disclosure, with base component, guide assembly and optional insertion mechanism, alone or in a system including an instrument, may be used in methods to guide access to other cavities, tracts, vessels or organs of the body, aside from gaining access to the kidney, such as procedures to gain access to peritoneal, abdominal, bronchial or thoracic cavities, vascular vessels, GI tract, uterine, uterus, bladder, lung and liver organs, etc. Any of the instruments according to the various embodiments described and other embodiments of the present disclosure, in addition to other instruments requiring guided access not specifically described herein, may be used with devices and methods according to the present disclosure. Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A device for guiding the insertion of an instrument having a longitudinal axis into a body of a patient at a targeted point of entry and along a path at a targeted insertion angle, the device comprising:
   a base component comprising a proximal surface, a distal surface, a lumen extending therethrough, a stationary housing portion, and a pull tab housing portion extending radially with respect to the stationary housing portion, the base component configured to be oriented and fixed in a first position, wherein the first position corresponds to the targeted point of entry; and
   a guide assembly, the assembly having a first element cooperating with the base component to orient the instrument with respect to the first position, a second element comprising a ball configured to be oriented and fixed in a second position wherein the second position corresponds to the targeted insertion angle, and a third element configured to translate the insertion angle to the instrument as the third element guides the instrument along the longitudinal axis into the body, the second element further comprising a pull tab extending within the pull tab housing portion of the base component;
   wherein:
   the second element and the proximal surface of the base component comprise a ball and socket arrangement;
   the pull tab is configured to be pulled along the pull tab housing portion radially away from the ball to frictionally fix a position of the ball with respect to the socket; and
   the guide assembly is configured to be removed from the stationary housing portion of the base component after removal of the instrument.

2. The device of claim 1, wherein the lumen is aligned in the first position during insertion, the distal surface configured to provide stable engagement of the device against the body during insertion, the guide assembly removably engageable with the proximal surface of the base component, the first element including a first guide hole in alignment with the lumen of the base component, the third element including a second guide hole configured to slidingly accommodate the instrument in alignment with the first guide hole and the lumen of the base component during insertion, and the second element comprising the first guide hole and the second guide hole.

3. The device of claim 2, wherein in the ball and socket arrangement, the ball of the second element including the first guide hole and the second guide hole in linear alignment and together forming a through lumen in the ball in alignment with the lumen of the base component, the ball adjustable in the socket to align the through lumen to the second position.

4. The device of claim 3, further comprising the instrument extendable through the through lumen of the ball and the lumen of the base component.

5. The device of claim 4, further comprising a guidewire extendable through a lumen of the instrument.

6. The device of claim 4, wherein the instrument includes an access needle.

7. The device of claim 2, further comprising an insertion mechanism affixed to the guide assembly, the insertion mechanism including an instrument holder, flexible wing portions and an insertion member, the wing portions extending at one end from the side of the guide assembly to another end fixed at sides of the instrument holder, the insertion member in operable arrangement with the instrument holder and wing portions, whereby movement of the insertion member flexes the wing portions and moves the instrument holder toward the base component and guide assembly in alignment with the first and second positions.

8. The device of claim 2, wherein alignment of the second element to the second position can be at any circumferential angle ranging from 0 to 360 degrees around an axis perpendicular to the first position and at any vertical angle ranging from 0 to 45 degrees away from such axis in a direction toward the body.

9. The device of claim 2, wherein one or both of the first and second guide holes comprise a radiopaque material.

10. The device of claim 1, wherein the distal surface of the base component is contoured to conform to the body of the patient.

11. The device of claim 1, wherein the distal surface of the base component includes an adhesive.

12. The device of claim 1, wherein pushing the pull tab towards the ball frictionally fixes a position of the ball, with respect to the socket.

13. A system for establishing guided access into the body of a patient at a targeted point of entry and along a path at a targeted insertion angle, the system comprising:
   an instrument having a longitudinal axis;
   a base component comprising a proximal surface, a distal surface, a lumen extending therethrough, a stationary housing portion, and a pull tab housing portion, the base component configured to be oriented and fixed in a first position, wherein the first position corresponds to the targeted point of entry; and
   a guide assembly, the assembly having a first element cooperating with the base component to orient the guide assembly with respect to the first position, a second element comprising a ball configured to be oriented and fixed in a second position wherein the second position corresponds to the targeted insertion angle and is linearly aligned with the first position, and a third element configured to translate the insertion angle to the instrument during entry into the body, the second element further comprising a pull tab extending along the pull tab housing portion of the base component;

wherein:

the second element and the proximal surface of the base component comprise a ball and socket arrangement;

the pull tab is configured to be pulled along a recess in the pull tab housing portion radially away from the ball to frictionally fix a position of the ball with respect to the socket; and the guide assembly is configured to be removed from the stationary housing portion of the base component after removal of the instrument.

14. A device for guiding the insertion of an instrument having a longitudinal axis into a body of a patient at a targeted point of entry and along a path at a targeted insertion angle, comprising:

a base component comprising a proximal surface, a distal surface and a lumen extending therethrough, the base component configured to be oriented and fixed in a first position, wherein the first position corresponds to the targeted point of entry; and a guide assembly, the assembly having a first element cooperating with the base component to orient the instrument with respect to the first position, a second element configured to be oriented and fixed in a second position wherein the second position corresponds to the targeted insertion angle, and a third element configured to translate the insertion angle to the instrument as the third element guides the instrument along the longitudinal axis into the body, the second element further comprising a pull tab comprising a plurality of perforations recessed within a pull tab housing portion of the base component;

wherein the second element and the proximal surface of the base component comprise a ball and socket arrangement; and wherein the pull tab is configured to be pulled radially away from the ball to frictionally fix a position of the ball with respect to the socket and wherein the guide assembly is configured to be removed from the base component after removal of the instrument.

* * * * *